US008626149B2

(12) United States Patent
Steenstra et al.

(10) Patent No.: US 8,626,149 B2
(45) Date of Patent: Jan. 7, 2014

(54) MONITORING AND TROUBLESHOOTING A MODULE ASSOCIATED WITH A PORTABLE COMMUNICATION DEVICE

(75) Inventors: Jack Steenstra, San Diego, CA (US); Guilherme Luiz Karnas Hoefel, San Diego, CA (US); Liren Chen, San Diego, CA (US); Kirk S. Taylor, San Diego, CA (US); Lucian Suta, Mission Viejo, CA (US); Yang Zhang, San Diego, CA (US)

(73) Assignee: QUALCOMM Incorporated, San Diego, CA (US)

(\*) Notice: Subject to any disclaimer, the term of this patent is extended or adjusted under 35 U.S.C. 154(b) by 965 days.

(21) Appl. No.: 11/959,083

(22) Filed: Dec. 18, 2007

(65) Prior Publication Data

US 2009/0156199 A1  Jun. 18, 2009

(51) Int. Cl.
*H04M 1/00* (2006.01)
*H04W 24/00* (2009.01)

(52) U.S. Cl.
USPC ........ 455/423; 455/556.1; 455/557; 128/903; 600/301

(58) Field of Classification Search
USPC ............... 455/423, 424, 425, 556.1, 557; 128/903; 600/300, 301
See application file for complete search history.

(56) References Cited

U.S. PATENT DOCUMENTS

| 6,725,061 | B1 * | 4/2004 | Hutchison et al. | 455/557 |
|---|---|---|---|---|
| 6,845,249 | B1 * | 1/2005 | Miller et al. | 455/556.1 |
| 7,062,260 | B2 * | 6/2006 | Vuori | 455/418 |
| 7,162,395 | B1 * | 1/2007 | Holmes et al. | 702/188 |
| 7,321,766 | B2 * | 1/2008 | Liu et al. | 455/425 |
| 7,599,717 | B2 | 10/2009 | Guthrie | |
| 7,617,423 | B2 * | 11/2009 | Patel et al. | 714/55 |
| 8,073,503 | B2 * | 12/2011 | Hoefel et al. | 455/575.1 |
| 8,170,609 | B2 * | 5/2012 | Hedtke et al. | 455/556.1 |
| 2001/0006891 | A1 | 7/2001 | Cho | |
| 2003/0162562 | A1 * | 8/2003 | Curtiss et al. | 455/556 |
| 2003/0176183 | A1 * | 9/2003 | Drucker et al. | 455/414.1 |
| 2004/0152457 | A1 * | 8/2004 | Goldstein et al. | 455/419 |
| 2004/0192274 | A1 * | 9/2004 | Vuori | 455/418 |
| 2004/0203726 | A1 * | 10/2004 | Wei | 455/423 |
| 2005/0014531 | A1 * | 1/2005 | Findikli | 455/557 |
| 2005/0101309 | A1 * | 5/2005 | Croome | 455/418 |
| 2006/0046651 | A1 * | 3/2006 | Hazell et al. | 455/41.2 |
| 2006/0234698 | A1 * | 10/2006 | Fok et al. | 455/425 |
| 2007/0015538 | A1 * | 1/2007 | Wang | 455/558 |

(Continued)

FOREIGN PATENT DOCUMENTS

| CN | 1841547 A | 10/2006 |
|---|---|---|
| CN | 1866853 A | 11/2006 |

(Continued)

OTHER PUBLICATIONS

International Search Report and Written Opinion—PCT/US2008/087174—ISA/EPO—Apr. 6, 2009.

*Primary Examiner* — Steven Kelley
(74) *Attorney, Agent, or Firm* — James T. Hagler

(57) ABSTRACT

Methods, apparatuses, and software to monitor, troubleshoot, or diagnose one or more specialty modules associated with a portable communication device are provided. The methods, apparatuses, and software identify the specialty module, obtain and execute procedures to monitor, test, or diagnose the specialty module. If unsatisfactory, error, defective or the like performance is identified, a solution is applied to correct the performance.

22 Claims, 6 Drawing Sheets

(56) References Cited

U.S. PATENT DOCUMENTS

| | | | |
|---|---|---|---|
| 2007/0072599 A1* | 3/2007 | Romine et al. | 455/423 |
| 2007/0099592 A1 | 5/2007 | Thome et al. | |
| 2007/0123174 A1* | 5/2007 | Wiessner et al. | 455/73 |
| 2007/0135092 A1* | 6/2007 | Pieronek et al. | 455/411 |
| 2007/0155332 A1* | 7/2007 | Burgan et al. | 455/67.11 |
| 2007/0207800 A1* | 9/2007 | Daley et al. | 455/425 |
| 2007/0243911 A1 | 10/2007 | Saito | |
| 2008/0004003 A1* | 1/2008 | Wulff et al. | 455/425 |
| 2008/0146276 A1* | 6/2008 | Lee | 455/556.1 |
| 2008/0220814 A1* | 9/2008 | Hedtke et al. | 455/556.1 |
| 2008/0242348 A1* | 10/2008 | Hsu | 455/556.1 |
| 2008/0311953 A1* | 12/2008 | Shen | 455/556.2 |
| 2009/0156200 A1* | 6/2009 | Ishii | 455/425 |
| 2010/0222648 A1* | 9/2010 | Tan | 600/301 |
| 2010/0317401 A1* | 12/2010 | Lee et al. | 455/557 |

FOREIGN PATENT DOCUMENTS

| | | |
|---|---|---|
| CN | 2869879 Y | 2/2007 |
| JP | 2001230725 A | 8/2001 |
| JP | 2007034468 A | 2/2007 |
| KR | 100575726 | 5/2006 |
| WO | WO2006057293 A1 | 6/2006 |
| WO | WO2007053329 | 5/2007 |
| WO | WO2007055884 A1 | 5/2007 |

* cited by examiner

MONITORING AND TROUBLESHOOTING A MODULE ASSOCIATED WITH A PORTABLE COMMUNICATION DEVICE

CLAIM OF PRIORITY UNDER 35 U.S.C. §119

None.

CLAIM OF PRIORITY UNDER 35 U.S.C. §120

None.

REFERENCE TO CO-PENDING APPLICATIONS FOR PATENT

None.

BACKGROUND

1. Field

The technology of the present application relates to modules associated with portable communication devices, and more specifically to monitoring and troubleshooting a module, such as a personal health module, associated with a portable communication device.

2. Background

Mobile computing devices are getting more capable with each new generation of technology. Mobile computing devices may generically be referred to as wireless devices, and include, for example, cellular telephones, wireless laptop computers, MP3 players (such as the IPOD®, by Apple, Inc.), electronic games, audio/video players, navigation devices (such as satellite position systems like the global positioning system), and the like. Moreover, as mobile devices become more and more ubiquitous in society, the distinctions and differences between various mobile computing devices are blurring. For example, many cellular telephones now contain capabilities for processing data typically associated with processing devices such as personal computers. Cellular telephones also double as digital cameras, video recorders and playback devices. Computers frequently contain voice communication capability and the like.

As wireless devices become more ubiquitous and robust, proper operation of the devices have become more critical to the user. Critical to the user may revolve around personal information, job information, or the like including, for example, medical information, navigational information, banking and financial information, and the like.

One useful way to increase the functionality of a wireless device is to provide a portable communication device portion that provides base functionality but can couple to one or more specialty modules, for example, a personal health module. Thus, the wireless device will have multiple and increased functionality but the base device can remain constant. In other words, using specialty modules provide a mechanism to increase the functionality of the wireless device while leaving the base portable communication device relatively unchanged.

As the uses of wireless devices increase, the need to monitor, diagnose, and troubleshoot operation of the portable communication device and the specialty modules associated with the wireless device increases. Thus, there is a need for improvements relating to monitoring, diagnosing, and troubleshooting a wireless device including the portable communication device and one or more specialty modules.

SUMMARY

Embodiments disclosed herein address the above stated needs by providing methods for monitoring, troubleshooting, or diagnosing specialty modules connected to portable communication devices. The methods comprise, for example, identifying a specialty module connected to the portable communication device from a plurality of specialty modules adapted to be connected to the portable communication device and obtaining monitoring, testing, or diagnostic procedures based on the specialty module identified. The obtained procedures are executed by the portable communication device to generate a report. Using the report, it is determined whether a solution exists and, if so, the solution is applied.

Embodiments disclosed herein address the above stated needs by providing a wireless device. The wireless device includes a portable communication device contained in a housing with a control processor for controlling, functions of at least fee portable communication device, a user interface to allow a user to interact with at least the portable communication device, transmit and receive circuits to provide modulation and demodulation of radio frequency signals between an antenna and the control processor and one or more specialty modules attachable to the portable communication device. A monitoring, troubleshooting, or diagnostic unit connected to the control, processor to monitor, troubleshoot, and diagnose the specialty module. The monitoring, troubleshooting, or diagnostic unit accesses a memory containing executable code for one or more monitoring, troubleshooting, or diagnostic procedures, wherein the monitoring, troubleshooting, or diagnostic unit accesses the memory to execute the one or more monitoring, troubleshooting, or diagnostic procedures.

DETAILED DESCRIPTION

The technology of the present application will now be explained with reference to the figures. While the description and figures specifically relate to a cellular telephone for a portable communication device and a personal health module, such as a blood glucose monitor, for the specialty module, one of ordinary skill in the art on reading the disclosure would now understand that other portable communication devices and specialty modules are possible. For example, other portable communication devices may include, wireless computers, handheld computers, electronic games, MP3 players, portable digital assistance, and the like. Other specialty modules may include, financial modules, navigation modules, combining two or more portable communication devices or the like (for example, a cellular telephone with an MP3 player). Moreover, the technology of the present application will be described with reference to exemplary embodiments thereof. The word "exemplary" is used herein to mean "serving as an example, instance, or illustration." Any embodiment described herein as "exemplary" is not necessarily to be construed as preferred or advantageous over other embodiments.

Moreover, unless explicitly stated, all provided examples should be considered exemplary.

Figure 1:
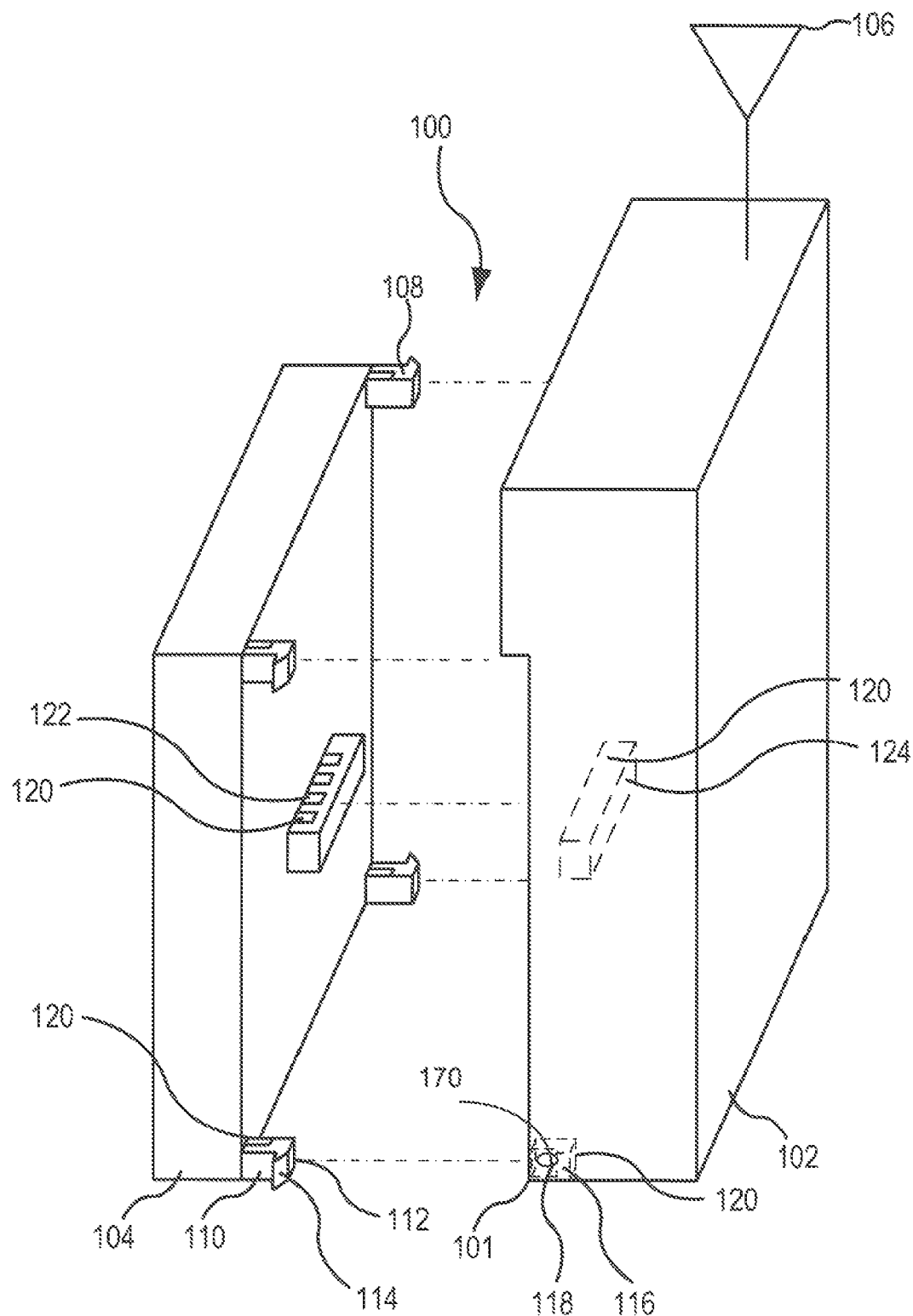
FIG. 1 is a functional block diagram of an exemplary wireless device using technology of the present application.

Referring now to FIG. 1, a wireless device 100 constructed, using the technology of the present application is illustrated. In this exemplary wireless device 100, wireless device 100 includes a portable communication device 102 and a specialty module 104. Wireless device 100 is shown partially exploded for convenience. Portable communication device 102 would have at least one radio frequency antenna 106, but may have multiple antennas. Frequently, portable communication device 102 will transmit and receive radio frequency signals over multiple operational frequencies that may require either multiple antennas or a single antenna that operates over the necessary frequencies. Portable communication, device 102 may consist of any number of devices such as, for example, a wireless computer, a portable digital assistant (such as a BLACKBERRY®, from Research in Motion, Ltd), a cellular telephone, or the like. Although shown and described as a portable communication device, one of ordinary skill in the art on reading the present application will now recognize that wireless device 100 may be a wired, (or a traditionally non-portable) device including a conventional computing device that is connected to a network via a conventional modem, ISP, or the like via a wired connection. For example, instead of a portable communication device, wireless device 100 may comprise a desktop computer.

Wireless device 100 as explained above also has one or more specialty modules (SMs) 104 attachable to portable communication device 102, although only one SM 104 is shown for convenience. Optionally, portable communication device 102 has a recess 101 to accommodate SM 104 such that wireless device 100 houses both portable communication device 102 and SM 104. SMs 104 may include, by way of non-limiting example, personal health modules, such as, a pulse meter, a blood glucose meter, a oxygen meter, a cardio monitor, etc. SMs 104 may include, by way of non-limiting example, application modules, such as, a navigation module, a financial module, a game module, a MPEG player, a MP3 player, etc. SMs 104 may be integrated into wireless device 100 or attachable to wireless device 100 as a plug-in module or the like, which would facilitate several SMs 104 being attachable to wireless device 100. SM 104 shown in FIG. 1 is removable from or attachable to wireless device 100 by, for example, a plurality of connections 108, which are shown as snap fit connection 108. As shown, snap fit connection 108 includes a protrusion 110 extending from SM 104 with a flared end 112 forming lip 114. Protrusion 110 and flared end 112 fit into a corresponding socket 116 in wireless device 100 having a shoulder 118. Protrusion 110 should be flexible to allow flared end 112 to pass shoulder 118 such that lip 114 and shoulder 118 abut to mechanically couple or snap fit SM 104 to portable communication device 102. Electrical connection could be by conductive traces 120 on the snap fitting or a separate tab 122 with conductive traces 120 fitting into a slot 124 with corresponding conductive traces 120. Electrical and mechanical coupling of SM 104 to portable communication device 102 should be arranged such that the electrical connection and mechanical connections facilitate connecting a plurality of SMs 104 to a plurality of portable communication devices 102. Thus, for example, portable communication device 102 may couple (electrically and mechanically) to a first blood glucose meter SM 104 and a second navigation module SM 104. Moreover, for example, first blood glucose meter SM 104 may couple (electrically and mechanically) to a cellular telephone portable communication device 102 or a personal computer portable communication device 102.

Alternatively to, for example, conductive traces 120 on tab 122 and corresponding conductive traces 120 in slot 124, SM 104 may be wirelessly connected to portable communication device 102. For example, SM 104 may include a radio frequency antenna 122b coupled to a corresponding radio frequency antenna 124b fanning a local wireless network between SM 104 and portable communication device 102. While any radio frequency protocols couple be used to couple radio frequency antenna 122b and 124b, low power radio frequency systems used for personal area networks are particularly suited for such applications. Some exemplary personal area network protocols include IEEE 802.15, Bluetooth, Zigbee to name but three examples personal area networks. However, other wireless protocols also could be used, such as those protocols more commonly associated with IEEE 802.11 of which will is but one example.

Wireless device 100 is described generally as a compact device for mobility, but one of ordinary skill is the art will recognize that wireless device 100 also may be a special processor uniquely designed for the above system.

Figure 2:
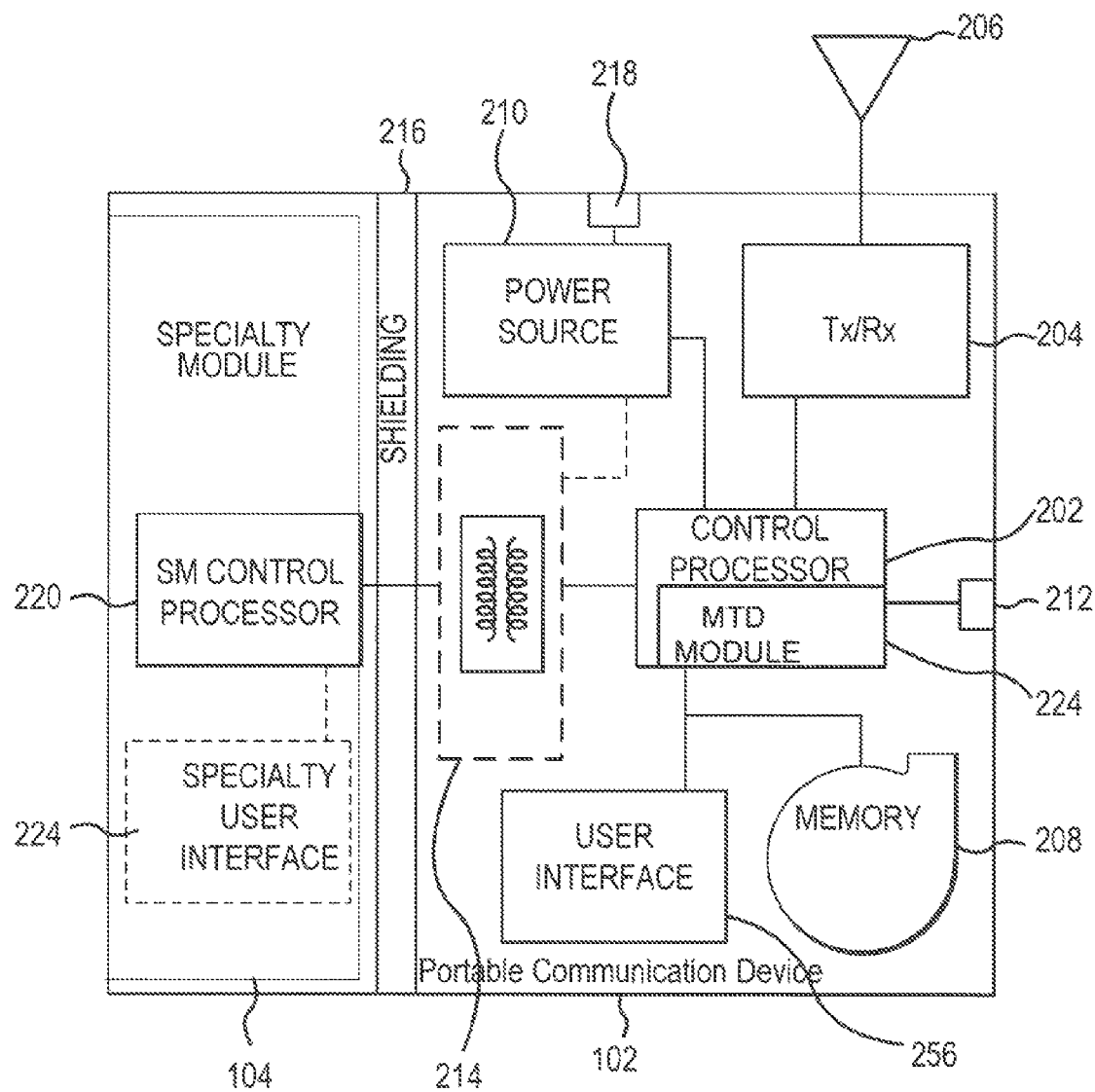
FIG. 2 is a is a functional block diagram of portable communication device and specialty module of FIG. 1.

Referring now to FIG. 2, a functional block diagram of portable communication device 102 and SM 104 are shown in more detail in an exemplary embodiment. Portable communication device 102 includes several components including a control processor 202. Control processor 202 controls the major functions of portable communication device 102 including providing computing functionality to process the inputs and/or data required for the operation of portable communication device 102. Transmit/receive circuitry 204 is connected to control processor 202 and antenna(s) 106. Transmit/receive circuitry 204 may be one or more actual circuits and may work over various protocols and wavelengths. Transmit/receive circuitry 204 functions typical of such components as used in wireless communications, such as modulating signals received from the control processor 202 that are to be transmitted from antenna 206, and demodulating signals received at antenna 206. The demodulated signal is provided to control processor 202.

Portable communication device 102 includes a user interface 256. User interface 256 may comprise a user interface typical of a cellular phone or typical of the wireless device, such as, for example, a keyboard, alphanumeric pad, mouse, track ball, touch screen, voice recognition, microphones, speakers, data ports, input ports, or the like. Optionally, as in this exemplary embodiment, user interface 256 may include features typical of SM 104. Alternatively, SM 104 may have, a separate user interface.

Portable communication device 102 includes a memory 208 connected to control processor 202. Memory 208 may store data and processing instructions necessary or convenient for operation of portable communication device 102. Memory 208 may include volatile and/or nonvolatile memory on any suitable media. Moreover, memory 208 may include a protected portion accessible only on entry of an authentication code, such as, for example, a password, or biometric data. Moreover protected portion may be encrypted. Memory 208 may store data relating to information recorded by SM 104 as well. For data contained in memory 208 relating to SM 104, the data may be stored in memory 208 as if memory 208 was a primary store of data, a backup store of data for a memory contained in SM 104 (not specifically shown), used to check data stored in primary memory, or the like.

Portable communication device 102 includes a power source 210. Power source 210 may be any conventional power source and is typically a battery pack. Power source 210 is connected to a recharge port 218 that is connectable to, for example, a wall socket, a car lighter, or the like. Portable communication device 102 also may include a data port 212 (data port 212 may sometimes be referred to as an input port 212 or an output port 212 depending on the context) connected to control processor 202. While not illustrated in FIG. 2, portable communication device 102 includes additional components and connections, such as, for example, cables, interfaces, circuit boards, and the like conventional in such devices for operation.

In some cases, it may be desirous to isolate operation of SM 104 and portable communication device 102. In those cases, portable communication device 102 may include an isolation circuit 214. Isolation circuit 214 provides electrical isolation between portable communication device 102 and SM 104 to inhibit failures or operations of portable communication device 102 from electrically interfering with SM 104. Alternatively, isolation circuit 214 may be contained in SM 104. Additionally, shielding 216, which may reside in portable communication device 102 or SM 104 may be provided to further isolate portable communication device 102 and SM 104. For example, shielding 216 may include electromagnetic shielding to inhibit radio frequency transmissions from antenna 106 or other RF transmission components from interfering with the SM 104 or the associated SM control processor 220. Types of electromagnetic shielding are generally well known in the art and will not be further explained herein. Shielding 216 may include beat shielding as is generally know in the art, such as, fiberglass insulation, phase change material insulations, or the like to regulate the temperature internal to SM 104. Heat shielding may be necessary in some cases where SM 104 requires operation in a controlled, temperature (additional temperature precautions are described below). Heat shielding may be particularly useful as portable communication device may include electronic components that generate sufficient heat to impact the SM 104 operation. Shielding 216 also may include sealing components such as a gasket or o-ring to provide a moisture barrier to inhibit moisture from impacting SM 104. Sealing components may include hermetic sealing components to reduce environmental impacts to SM 104. Sealing components additionally may include antibacterial or anti microbial components and the like.

As shown, control processor 202 contains a monitoring, troubleshooting, and diagnostic (MTD) component or unit 224. While shown integrated in control processor 202, MTD unit 224 may be a separate component integrated with portable communication device 102. Operation of MTD unit 224 will be explained further below.

Figure 3:
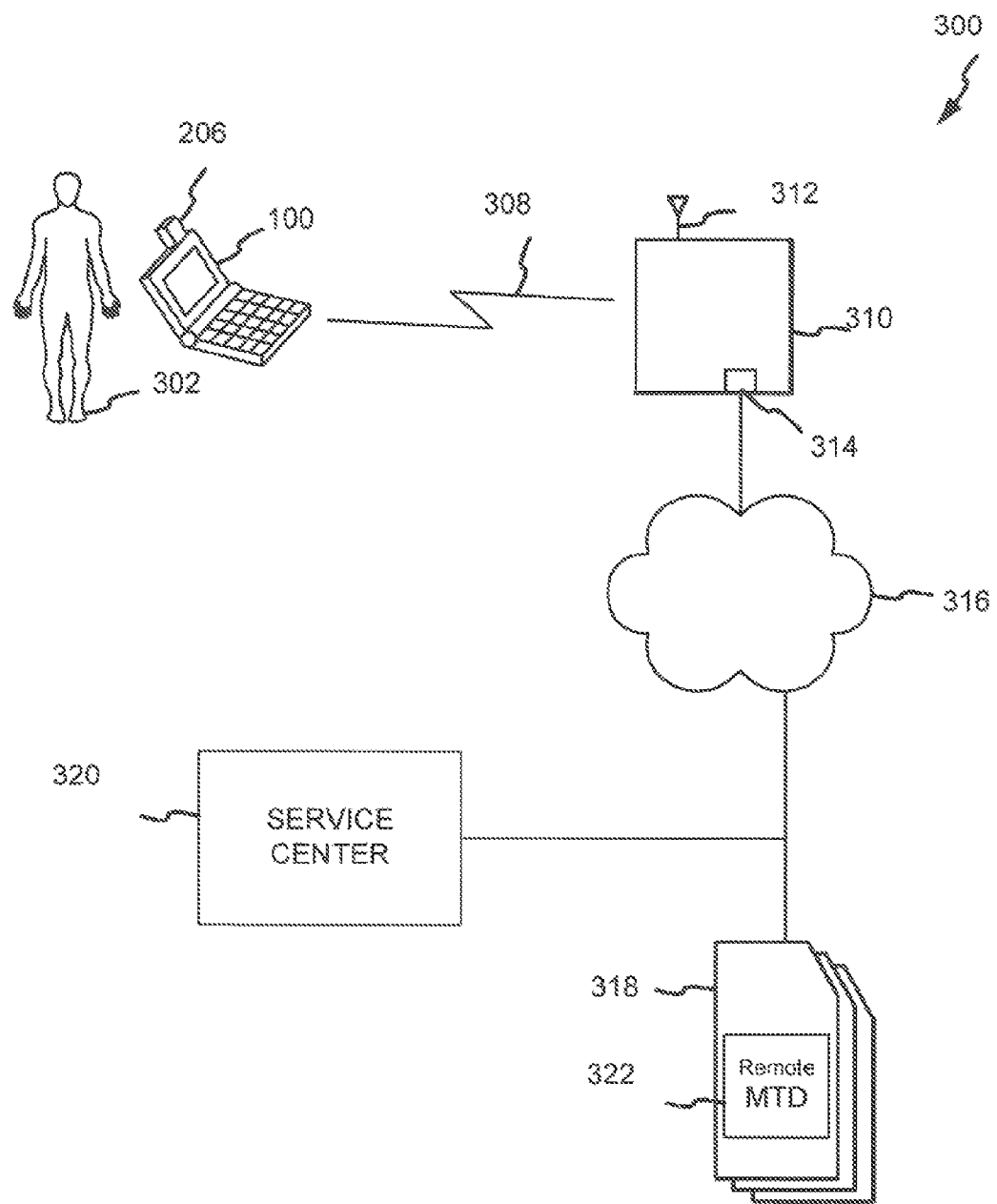
FIG. 3 is a functional block diagram of a communication, system using the technology of the present application.

Referring now to FIG. 3, a wireless communication system 300 is provided. Wireless communication system 300, for example, may be a cellular communication system, such as, for example CMDA, GSM, or the like, in this system, wireless device 100 communicates, through antenna 206 for example, via a data link 308 to a base station 310. Base station 310 has an antenna 312. Antenna 206 and base station antenna 312 can transmit and receive respective radio frequency signals to allow data transfer between wireless device 100 and base station 310. Base station 310 may have a network interface 314 such that it is interconnected to a network 316. Network 316 may be several networks, but network 316 will be described as a single network for convenience. Network 316 typically is connected to servers 318 and/or service centers 320 as necessary. Servers 318 may include a remote monitoring, troubleshooting, and diagnostic (Remote MTD) component or unit 322, the operation of which will be explained further below.

Wireless communication system 300 is shown with a single wireless device 100 connected to a single base station 310. It is envisioned, however, that wireless communication system 300 would support multiple wireless devices 304, multiple base station 310 and multiple networks as a matter of design choice. In these instances, it may be beneficial to incorporate security measures in the system and assign unique identifiers to the remote stations.

As mentioned above, for a cellular telephone portable communication device 102 associated with wireless device 100, it may communication with base station 310 using a conventional protocol, such as CDMA or the like, although any analog or digital protocol is acceptable. Moreover, while described using a cellular network for communication and data transfer between wireless device 100 and base station 310, other wireless or wired networks are possible.

As will be further explained in exemplary diagrams illustrating the operation of the technology, it can be appreciated that wireless communication system 300 provides MTD unit 224 to provide local monitoring, troubleshooting, and diagnostics locally of the wireless device 100 including portable communication device 102 and SM 104. Wireless communication system 300, however, additionally provides Remote MTD unit 322 to provide remote monitoring, troubleshooting, and diagnostic support to wireless device 100. Remote MTD 322 may provide back-up functionality for MTD unit 224 as well as augmented and/or different monitoring, troubleshooting, and diagnostic functions that wireless device 100 may not have the capacity or speed to perform.

Figure 4:
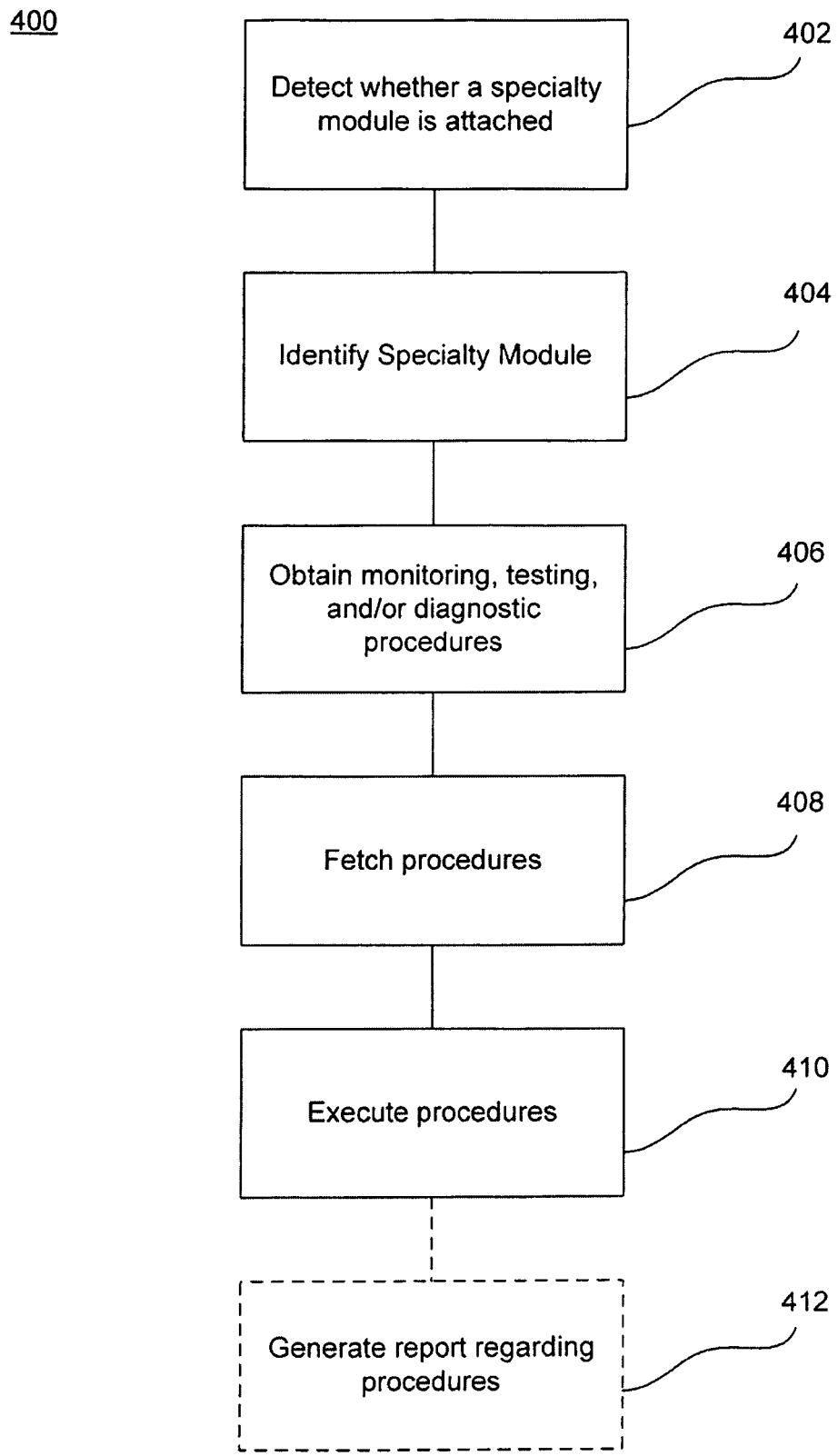
FIG. 4 is a flow chart diagram illustrating the operational steps of an exemplary embodiment.

Referring now to FIG. 4, an exemplary flow chart 400 illustrating one possible operation of an embodiment of the technology of the present invention. The operations described here and below provide step by step illustrations of operation. However, one of ordinary skill in the art would recognize now on reading the disclosure that these may be other, more, or less steps in the disclosed or alternative orders are possible. First, at step 402, MTD 224 detects whether a SM 104 is connected to a portable communication device 102. Detecting SM 104 may include mechanical means 170, such as a switch or other mechanical switch connection (mechanical means 170 is shown as a switch depressed by protrusion 110), and/or electrical connectivity, such as through conductive traces 120 on the snap fitting or a separate tab 122 with conductive traces 120 fitting into a slot 124 with corresponding conductive traces 120. Detecting SM 104 may in combination or alternatively occur when user 302 inputs through the user interface or the like, that a SM 104 is connected. Next, at step 404, MTD 224 determines or identifies SM 104. Determining or identifying SM 104 may occur as SM 104 sends a positive indication of what type of module it is, such as, for example, a financial module, a cardio module, or the like, alternatively, control processor 202 may send a polling signal or interrogation signal requesting the identification information from SM 104. Alternatively still or in some combination with the aforementioned, user 302 may input the type of module manually through a user interface. As can be appreciated from the above, different SMs 104 may be designed for connect with portable communication device 102; therefore, for MTD 224 to run proper tests or the like, it likely should first identify the module connected. For example, MTD 224 may have a first set of tests or the like for a personal health module and a second set of tests of the like for a navigation module. Once identified, MTD 224 obtains testing, monitoring, and/or diagnostic procedures, step 406. The procedures may be stored, within MTD 224. Optionally, the procedures may be fetched from memory 208 or from servers 318, step 408. Once obtained, the testing, monitoring, and/or diagnostic procedures are executed on the identified SM 104, step 410. After execution, optionally, a report is generated regarding the procedures, step 412. The report simply may be identification of deficiencies, unsatisfactory performance, errors, issues or the like associated with specialty module. Alternatively still, the MTD process may be remotely invoked by a network based service provider based on preset conditions, such as, for example, when a user initiates a session by signing in or the like, due to a period of inactivity of the specialty module for a period exceeding a predetermined threshold, based upon a reported problem from the user of the specialty module or the like, or upon the reception of unusual data.

Testing, monitoring, or diagnosis of SM 104 may result from standard procedures for all modules or be specifically related to the type module involved. Some test include, for example, mechanical connection, tests, electrical connection tests, software operation diagnostic tests, providing test signals and receiving proper return signals, or the like. Additional, and non-limiting, examples of types of testing and diagnostics include service availability testing (verifying the availability of network based services from the user's location); performance testing such as response time, available throughput, or the like; usage tracking logs; and security reporting, such as failed logins, suspicious packets from the network and certain unusual subscriber behaviors; and configuration and version testing.

Figure 5:
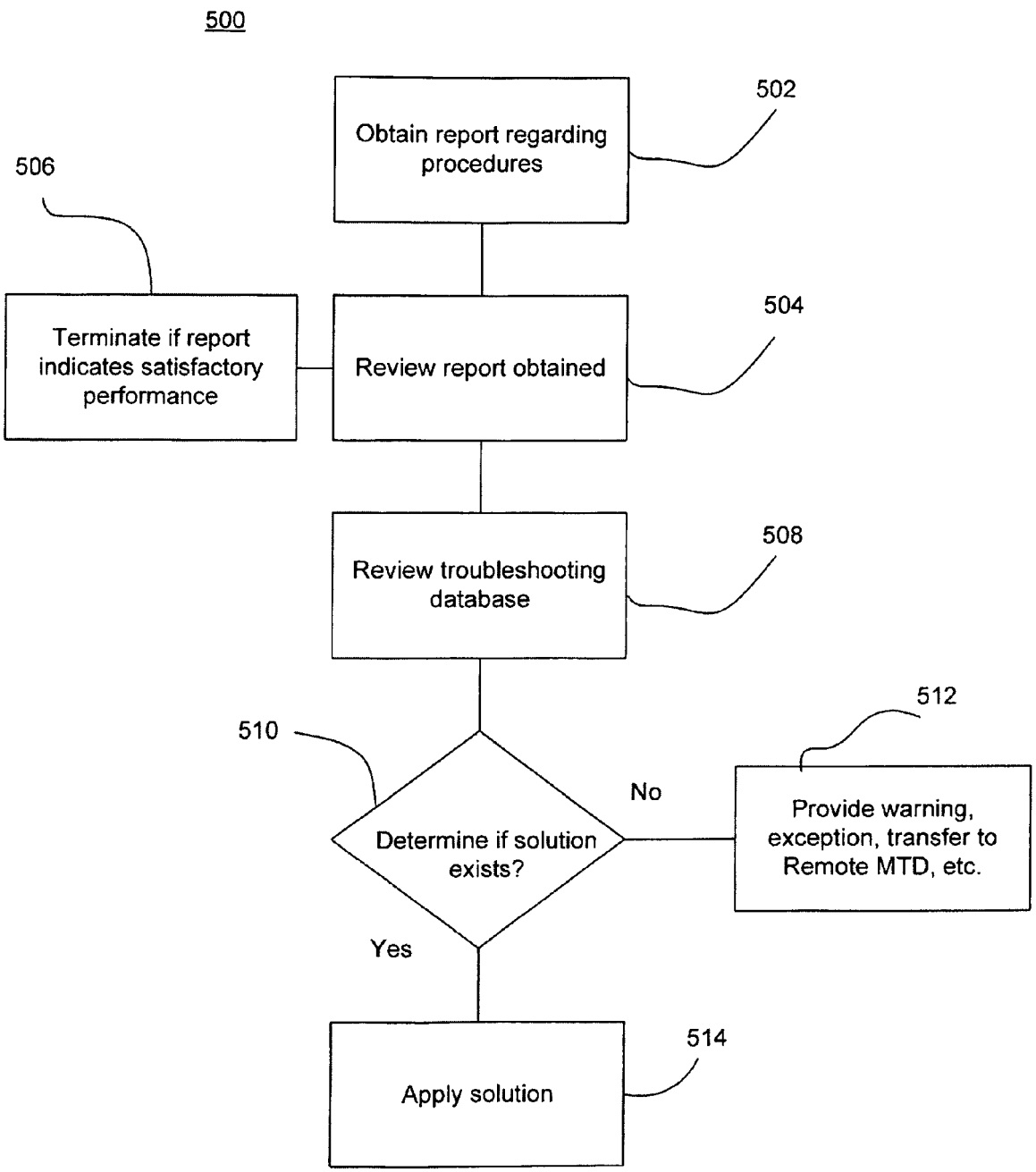
FIG. 5 is a flow chart diagram illustrating the operational steps of an exemplary embodiment.

Referring now to FIG. 5, an exemplary flowchart 500 is provided illustrating one possible operation of an embodiment of the technology of the present invention. First, the report regarding the testing, monitoring, and/or diagnostic procedures is obtained, step 502. The report may be contained in local or remote memory. The control processor 202 reviews the report to determine whether the SM 104 is operating satisfactory, step 504. If the report indicates the SM 104 is operating satisfactory, the process terminates, step 506. If the report indicates one or more non-satisfactory results, the control processor 202 reviews a troubleshooting database in memory (local or remote), step 508, and determines whether a potential, solution to the one or more non-satisfactory result, step 510. If a solution is not available, a warning or exception report may be, for example, communicated to the user 302, step 512. Alternatively, the procedures may be transferred to a remote system, see below (which may include escalating the issue to a human technician for trouble shooting). If a potential solution is available, the solution is applied, step 514. Such solution may involve numerous troubleshooting and corrective procedures and steps such as, for example, powering down the SM 104 and restarting the SM 104, booting the processors, installing a patch, transferring information and application between processors using simple network management protocols, downloading new software, updating versions, or the like as are generally known in the art.

Figure 6:
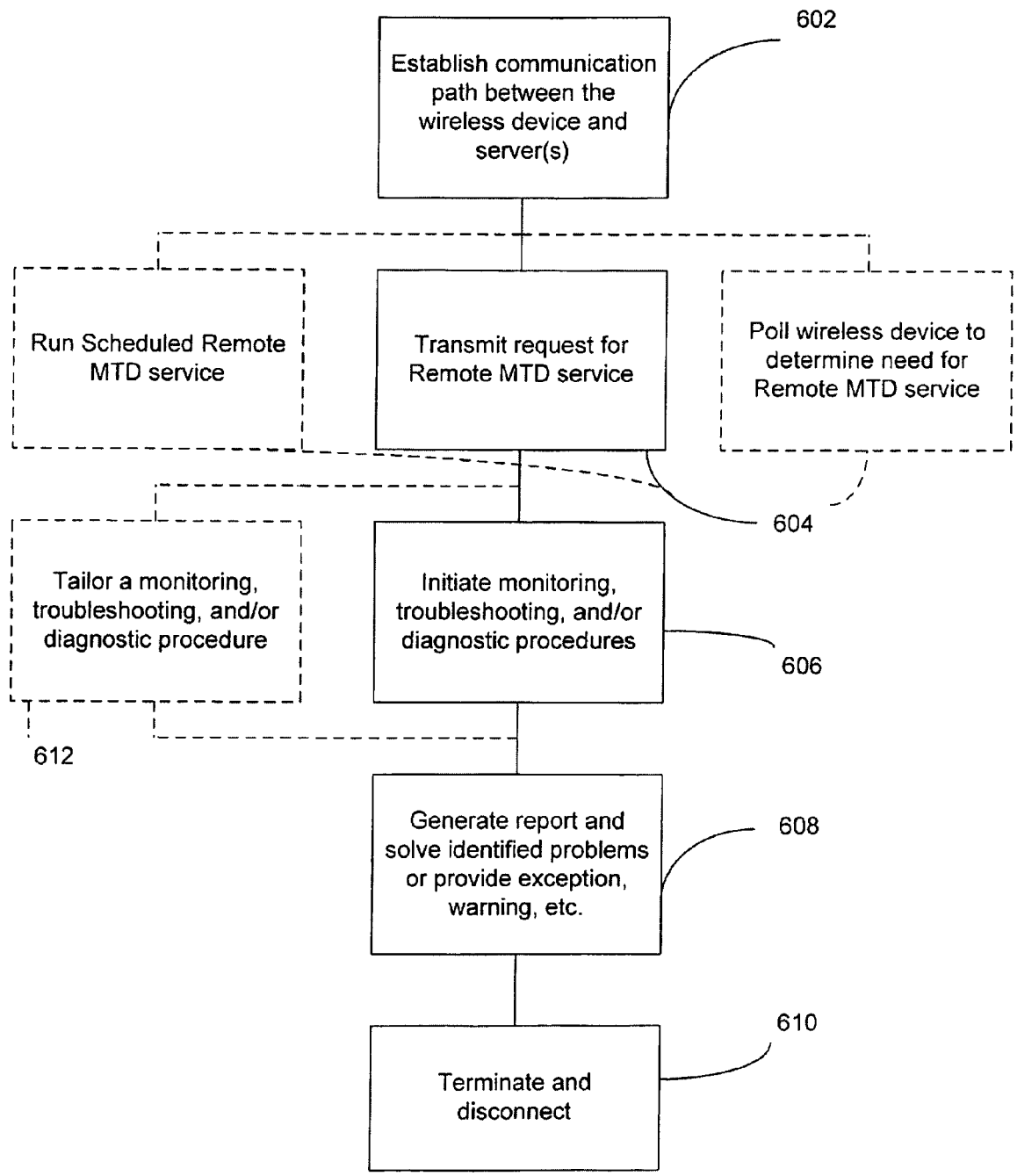
FIG. 6 is a flow chart diagram illustrating the operational steps of an exemplary embodiment.

While MTD unit 224 may be completely installed on a portable unit, the portable unit limitations may require MTD unit 224 to be limited due to constraints associated with processing power, costs, and the like related to the portable communication device. Thus, the technology of the present application provides a Remote MTD unit 322. Referring now to FIG. 6, an exemplary flowchart 600 is provided illustrating one possible operation of an embodiment of the technology of the present invention. First, a communication path is established between the wireless device and the servers, step 602. The communication path may be established, for example, by the wireless device calling the servers, the servers calling the wireless device, or the like depending on the actual network protocols recognizing that calling is typically associated with cellular networks, such as CDMA or GSM networks. Next, a signal is transmitted to Remote MTD unit 322 requesting testing, monitoring, and/or diagnostic procedures, step 604.

The signal transmitted to Remote MTD unit 322 may be initiated by the wireless device to for a variety of reasons including, for example, the MTD unit 224 identified, but could not resolve a problem, the MTD unit 224 is not operating correctly, the MTD unit 224 did not identify a problem although the module is not working properly. Alternatively, Remote MTD unit 322 may poll wireless devices to see if services are necessary and/or the services may be scheduled in advance. Once requested, Remote MTD unit 322 would initiate monitoring, troubleshooting, and/or diagnostic procedures similar to those described above in relation to FIG. 4, step 606. Next, remote MTD unit 322 would generate a report from the procedures and solve the identified issues similar to the operation described in FIG. 5, step 608. Once the solution is presented, the process would terminate by disconnecting the connection, step 610. Alternatively, as shown by the alternative flow path in dashed lines, Remote MTD 322 would receive information generated by MTD 224, step 612. Based on the information received, Remote MTD 322 may tailor a testing procedure or protocol, step 614. Once developed, control would continue with initiating the testing procedure at step 606.

Although described, as Remote MTD 322 accessible via a network connection. One of ordinary skill in the art on reading the disclosure would now recognize that Remote MTD unit 322 may be located on a general purpose computer such as, for example, a conventional laptop or desktop computer or the like. SM 104 may be connected to Remote MTD unit 322 via a conventional connection from SM 104 to the general purpose computer. The connection may be a wired connection, such as a plug in port, a universal serial bus, or the like or a wireless connection, such as bluetooth or the like.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the embodiments disclosed herein may be implemented or performed with a general purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, hut in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A method for diagnosing specialty modules connected to portable communication devices, comprising:
   detecting a specialty module connected to a portable communication device, wherein the specialty module is removably connectable to the portable communication device and is a personal health module selected from a group consisting of a pulse meter, a blood glucose meter, an oxygen meter, and a cardio monitor;
   identifying the specialty module connected to the portable communication device from a plurality of specialty modules adapted to be connected to the portable communication device;
   obtaining a diagnostic procedure based on the specialty module identified;
   executing, at the portable communication device, the obtained diagnostic procedure to diagnose the identified specialty module;
   generating a report based on the executed diagnostic procedure;
   first determining from the report whether the specialty module has unsatisfactory performance;
   second determining if a solution to the unsatisfactory performance exists by reviewing a troubleshooting database in memory; and
   if a solution exists, applying the solution.

2. The method of claim 1 wherein the second determining if a solution to the unsatisfactory performance exists comprises checking a memory of the portable communication device for the solution.

3. The method of claim 2, further comprising providing a warning when the second determining if a solution to the unsatisfactory performance determines a solution does not exist in the memory.

4. The method of claim 1, further comprising:
   establishing a communication link to a server when the second determining if a solution to the unsatisfactory performance determines a solution does not exist in the memory; and
   third determining if a solution to the unsatisfactory performance exists at the server.

5. The method of claim 1, wherein obtaining the diagnostic procedure comprises fetching the diagnostic procedure from a memory of portable communication device.

6. The method of claim 1, wherein obtaining diagnostic procedure comprises:
   establishing a communication link to a server; and
   fetching the diagnostic procedure from the server.

7. The method of claim 1, wherein the method of detecting is selected from the group consisting of: manually inputting the specialty module using a user interface, detecting a mechanical switch, and detecting an electrical connection.

8. The method of claim 1, further comprising diagnosing performance of the portable communication device.

9. The method of claim 1, wherein if the second determining if a solution to the unsatisfactory performance determines a solution does not exist in the memory, then the method further comprises alerting a service provider.

10. A wireless device, comprising:
    a portable communication device contained in a housing;
    a control processor contained in the housing for controlling functions of at least the portable communication device;
    a user interface connected to the control processor to allow a user to interact with at least the portable communication device;
    transmit and receive circuits to provide modulation and demodulation of radio frequency signals between an antenna and the control processor;
    a specialty module removably connectable to the portable communication device, wherein the specialty module is a personal health module selected from a group consisting of a pulse meter, a blood glucose meter, an oxygen meter, and a cardio monitor;
    means for detecting whether the specialty module is connected;
    a diagnostic unit connected to the control processor to diagnose the specialty module; and
    a memory containing executable instructions, wherein the diagnostic unit accesses the memory to execute the instructions, wherein the instructions are configured to:
       identify the specialty module connected to the portable communication device from a plurality of specialty modules adapted to be connected to the portable communication device;
       obtain a diagnostic procedure based on the specialty module identified;
       execute, at the portable communication device, the obtained diagnostic procedure;
       generate a report based on the executed diagnostic procedure;
       first determine from the report whether the specialty module has unsatisfactory performance;
       second determine if a solution to the unsatisfactory performance exists by reviewing a troubleshooting database in memory; and
       if a solution exists, apply the solution.

11. The wireless device of claim 10, wherein the means for detecting whether the specialty module is connected is selected from the group consisting of: a mechanical switch, an electro-mechanical switch, and an electrical connection.

12. The wireless device of claim 10, wherein the transmit and receive circuits communicate with a remote diagnostic unit residing in a server remote from the wireless device.

13. The wireless device of claim 12 wherein the server remote from the wireless device comprises a general purpose computer.

14. The wireless device of claim 12, wherein the transmit and receive circuits communicate to the remote diagnostic unit through a network selected from the group of networks consisting of: a wireless network, a PSTN network, a local area network, a wide area network, a WiFi network, a WiMax network, and a lower power radio frequency network.

15. The wireless device of claim 12 wherein the memory resides at the server.

16. The wireless device of claim 15 wherein the memory resides in the wireless device and at the server.

17. The wireless device of claim 11, wherein the removably connectable specialty module comprises one of a plurality of removably connectable specialty modules.

18. A wireless device, comprising:
a portable communication device contained in a housing;
means for controlling functions of at least the portable communication device;
means for interfacing with the means for controlling the at least the portable communication device;
means for transmitting and receiving radio frequency signals between an antenna and the control processor;
a specialty module that is a personal health module selected from a group consisting of a pulse meter, a blood glucose meter, an oxygen meter, and a cardio monitor;
means for attaching the specialty module and the portable communication device;
means for detecting whether the specialty module is connected;
means for diagnostic testing connected to the control processor to diagnose the specialty module; and
a memory containing executable instructions, wherein the diagnostic unit accesses the memory to execute the instructions, wherein the instructions are configured to:
identify the specialty module connected to the portable communication device from a plurality of specialty modules adapted to be connected to the portable communication device;
obtain a diagnostic procedure based on the specialty module identified;
execute, at the portable communication device, the obtained diagnostic procedure;
generate a report based on the executed diagnostic procedure;
first determine from the report whether the specialty module has unsatisfactory performance;
second determine if a solution to the unsatisfactory performance exists by reviewing a troubleshooting database in memory; and
if a solution exists, apply the solution.

19. The wireless device of claim 18 wherein the specialty module comprises one of a plurality of specialty modules.

20. The wireless device of claim 18 wherein the means for diagnostic testing is connected to the means for controlling through a network.

21. The wireless device of claim 20, wherein the network is a low power radio frequency network.

22. A non-transitory computer readable storage medium having stored thereon processor-executable software instructions configured to cause a processor of a portable communication device to perform operations comprising:
detecting a specialty module connected to the portable communication device, wherein the specialty module is removably connectable to the portable communication device and is a personal health module selected from a group consisting of a pulse meter, a blood glucose meter, an oxygen meter, and a cardio monitor;
identifying the specialty module from a plurality of specialty modules adapted to be connected to the portable communication device;
obtaining a diagnostic procedure based on the specialty module identified;
executing the diagnostic procedure to diagnose the identified specialty module;
generating a report based on the executed diagnostic procedure;
first determining from the report whether the specialty module has unsatisfactory performance;
second determining if a solution to the unsatisfactory performance exists by reviewing a troubleshooting database in memory; and
applying the solution if it exists.

* * * * *